US008342370B2

(12) United States Patent
Ross et al.

(10) Patent No.: US 8,342,370 B2
(45) Date of Patent: Jan. 1, 2013

(54) DOSAGE DISPENSING CANISTER

(75) Inventors: Calvin John Ross, Norwich (GB); Steven John Sansom, Norwich (GB)

(73) Assignee: Norwich Pharma Technologies Limited, Norwich (GB)

( * ) Notice: Subject to any disclaimer, the term of this patent is extended or adjusted under 35 U.S.C. 154(b) by 848 days.

(21) Appl. No.: 12/438,787

(22) PCT Filed: Aug. 21, 2007

(86) PCT No.: PCT/GB2007/003198

§ 371 (c)(1),
(2), (4) Date: Feb. 25, 2009

(87) PCT Pub. No.: WO2008/025953

PCT Pub. Date: Mar. 6, 2008

(65) Prior Publication Data

US 2009/0326442 A1 Dec. 31, 2009

(30) Foreign Application Priority Data

Aug. 26, 2006 (GB) .................................. 0616918.9

(51) Int. Cl.
*B65D 88/54* (2006.01)
*B67B 1/00* (2006.01)
*A61M 11/00* (2006.01)
*A61M 35/00* (2006.01)

(52) U.S. Cl. ..................... 222/320; 222/43; 222/153.11; 222/153.07; 128/200.23; 128/203.15; 604/298

(58) Field of Classification Search .................. 222/320, 222/153.05, 153.11, 43, 153.06, 153.07, 222/153.13, 153.09; 128/203.15, 200.23, 128/200.22, 200.14; 604/294, 295, 296, 604/297, 298, 299, 300, 301, 302
See application file for complete search history.

(56) References Cited

U.S. PATENT DOCUMENTS

| | | | |
|---|---|---|---|
| 1,393,720 A | 10/1921 | Lomas et al. | |
| 3,199,510 A * | 8/1965 | Sinai | 601/162 |
| 4,946,069 A * | 8/1990 | Fuchs | 222/43 |
| 5,284,132 A | 2/1994 | Geier | |
| 5,289,818 A * | 3/1994 | Citterio et al. | 128/200.14 |
| 5,427,280 A * | 6/1995 | Fuchs | 222/320 |
| 5,460,171 A * | 10/1995 | Pesenti et al. | 128/200.23 |
| 5,584,417 A | 12/1996 | Graf et al. | |
| 6,789,750 B1 | 9/2004 | Heldt | |
| 7,213,726 B2 * | 5/2007 | Rossignol | 222/153.13 |

(Continued)

FOREIGN PATENT DOCUMENTS

DE 0311863 4/1989

(Continued)

*Primary Examiner* — Kevin P Shaver
*Assistant Examiner* — Stephanie E Williams
(74) *Attorney, Agent, or Firm* — Renner, Otto, Boisselle & Sklar, LLP

(57) ABSTRACT

A one dose at a time, non-pressurized fluid dispensing canister from which the or each dose is dispensed as a result of two surfaces (21, 22) of the canister moving towards one another under the control of the user, wherein the canister incorporates a mechanism which, once a first dose has been dispensed, automatically prevents any further dispensing movement of the surfaces (21, 22) (in the case where the canister is a one-dosage only canister) or (where the canister is a multiple-dosage-dispensing canister) allows such movement only after the two surfaces (21, 22) have first been moved in a direction or directions other than that which alone caused the first dose to be dispensed.

16 Claims, 2 Drawing Sheets

U.S. PATENT DOCUMENTS 7,520,406 B2 * 4/2009 Jaichandra et al. ............ 222/47

FOREIGN PATENT DOCUMENTS

| | | |
|---|---|---|
| EP | 0311863 | 4/1989 |
| EP | 0611035 | 1/1994 |
| FR | 2883850 | 10/2006 |
| GB | 2187388 | 1/1987 |
| WO | 98/30335 | 7/1998 |

* cited by examiner

SECTION A-A

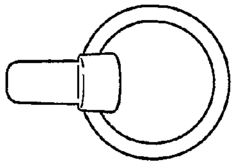
FIG. 8
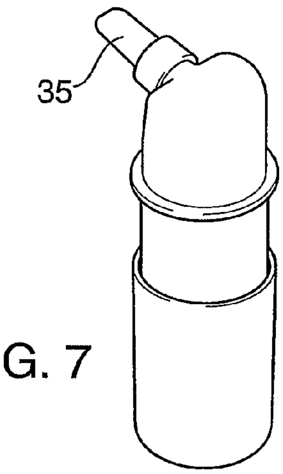
FIG. 7
FIG. 13
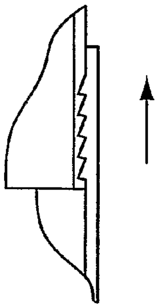
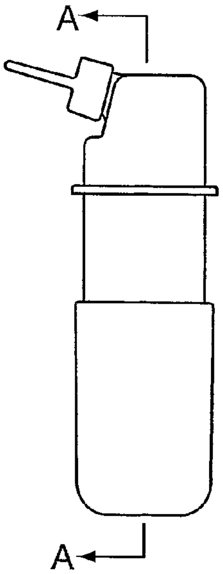
FIG. 9
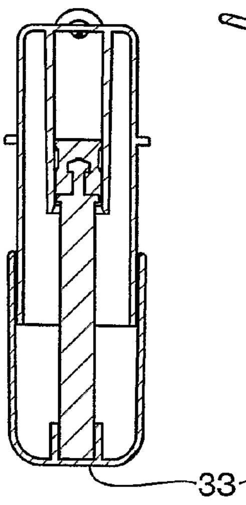
SECTION A-A
FIG. 10
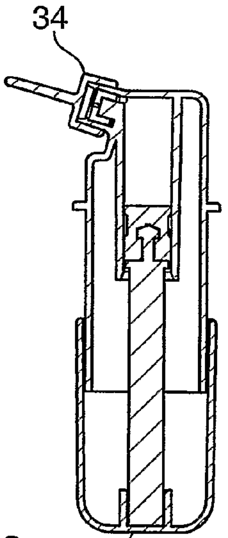
SECTION C-C
FIG. 11
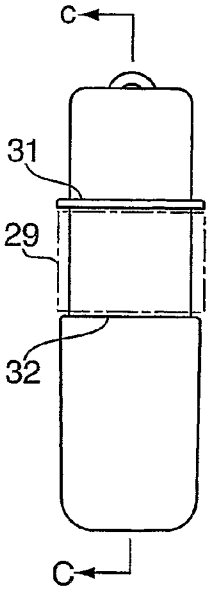
FIG. 12

DOSAGE DISPENSING CANISTER

This application is a national phase of International Application No. PCT/GB2007/003198 filed Aug. 21, 2007 and published in the English language.

FIELD OF THE INVENTION

The invention relates to an improved form of dosage dispensing canister and is particularly applicable to multiple-dosage canisters intended to dispense narcotic drugs in spray formulations suitable for sublingual delivery.

Fentanyl and cannabis are two examples of such drugs and their formulation for inhalation, oral lozenge delivery, or a sublingual use is well known. Equally well known are a plurality of approaches to the delivery problem as such. None of these solves the dangers inherent in potent controlled drugs such as those exemplified above whose misuse can lead to undesirable and indeed life-threatening side effects.

State of the Art as Known to the Applicant

Metal canisters are inherently not suitable for narcotic formulations because of the tendency of the canister in the area to corrode with time. Internal coating treatments may prove of use, but these are costly and are not immune to degradation. Metal canisters can also easily be tampered with to drain their contents because their walls are notoriously thin and this is especially the case with pressurised-propellant containing canisters.

Valves with multi polymer/metal springs to give metered dosages are available in various build options but these can require of the order of up to ten or more components. The risks of failure with repeated use are clear. Any metal components again are at risk of attack from the canister contents.

It is especially dangerous to try to package potent narcotic drugs in propellant-driven containers because any failure or puncture of the unit could automatically vent the contents into the room with dangerous and obvious inhalation risk. Furthermore, it is known that the valve assemblies in propellant-driven containers occasionally malfunction, and stick in an open position. This results in a continuous release of product, rather than in a dose-controlled fashion. The dangers of this when the product is a narcotic drug are self-evident.

Non-pressurised pumps attract the same complication objections as valve products. Separate actuators are common but these can be removed or can fall off. They may also cause the product to be sprayed in the wrong direction.

Lock out systems have been proposed by various workers but these are complex and typically incorporate electronic feedback systems, all of which again can go wrong; and whilst multiple dose packs are an attractive sale item in the (illegal) drug market, if anyone stands any reasonable chance of accessing all such pack contents then an inadvertent overdose can quickly follow.

There is finally the issue of priming which overshadows all these known proposals. Many of the proposers of aerosol and pump driven systems offer multi dose models in the belief that the products will hold prime during storage. This is not the case. All packs—in particular those incorporating dip tubes—will lose prime over time and will require up to (say) three actuations to reach the correct dose stated on the packs. The dangers are clear.

SUMMARY OF THE INVENTION

The invention seeks to provide a single-dosage or multi-dosage dispensing canister, especially but not only applicable to the safe dispensing of potent narcotics, in which the risks discussed above are minimised to enable safe measured doses to be administered to patients.

Accordingly, the invention provides a one dose at a time, non-pressurised fluid dispensing canister from which fluid is dispensed as a result of two surfaces of the canister moving, from a non-dispensing starting position, towards one another under the control of a user; said surfaces comprising the respective opposite end region surfaces of a two-portion canister one of whose portions telescopes within the other; characterised in that the canister incorporates a mechanism which, once a first dose has been dispensed, acts to prevent any subsequent attempted movement of the said surfaces into or towards their non-dispensing starting position.

In an alternative embodiment, the invention provides a one dose at a time, non-pressurised fluid dispensing canister from which the or each dose is dispensed as a result of two surfaces of the canister moving towards one another under the control of the user; characterised in that the canister incorporates a mechanism which, once a first dose has been dispensed, automatically prevents any further dispensing movement of the said surfaces (in the case where the canister is a one-dosage only canister) or (where the canister is a multiple-dosage-dispensing canister) allows such movement only after the two surfaces have first been moved in a direction or directions other than that which alone caused the first dose to be dispensed; or after the removal—or after a further dosage-allowing movement—of a portion of the canister has occurred.

Preferably, the surfaces comprise the respective opposite end region surfaces of a two-portion canister one of whose portions telescopes within the other. More preferably, the telescoped canister portions incorporate a one-way ratchet mechanism, which, once they are assembled to form the canister, resists any subsequent attempt to disassemble them. Most preferably, there are multiple engaging ratchet teeth thus allowing a single dose to be dispensed in progressive stages.

In any of these aspects, it is preferable that multiple doses can be dispensed after the first dose by imparting a twist-and-push relative movement to the canister surfaces each time a subsequent dose is desired to be dispensed. Preferably, the last such twist-and-push movement locks the canister portions. More preferably, the last such twist-and-push action either closes the orifice of the canister from which the fluid has been expelled and/or automatically ejects from the canister the orifice—containing portion thereof.

Included within the scope of the invention is a canister substantially as described herein with reference to and as illustrated in any appropriate combination of the accompanying drawings.

Also included within the scope of the invention is a drug dispensing canister constructed as described herein.

The embodiment of the invention to be described herein is especially suitable to sublingual delivery and is deliberately restricted to a dose pack size of two therapeutic doses only. Its design is inherently simple but leak-free and is readily portable, and its contents can be dispensed and directed with accuracy. It incorporates a mechanism which makes it impossible for the second dose to be delivered without first having exhausted the first dosage and then imparting a specific movement to the canister portions before the second dosage will be expelled at all.

The scope of the invention is defined in the claims and one particular embodiment of it will now be described in detail with reference to the accompanying drawings.

BRIEF DESCRIPTION OF THE DRAWINGS

In these drawings:

FIGS. 1 though 6 show a two-dosage container, embodying the invention, in conventional serial orthogonal projectional views in which

FIGS. 7 through 12 show similarly conventionally drawn views of a second, one-dosage-only, embodiment of the invention in which FIGS. 10 and 11 are respectively sections along the line A-A of FIG. 9 and the line c-c of FIG. 12; and FIG. 13 is a scrap section detail showing the one-way ratchet mechanism used in either of these embodiments.

DESCRIPTION OF THE PREFERRED EMBODIMENTS

Both embodiments consist of non-metallic materials and comprise essentially a circular-cylindrical elongated canister whose two half-portions telescope. These canisters are relatively small in size so as to be readily pocketed. Each contains a measured dosage of potent narcotic in fluid form and each is initially sheathed in suitable tamper-evident collar shields which must be removed before any dosage can be dispensed from the canister.

Figure 3:
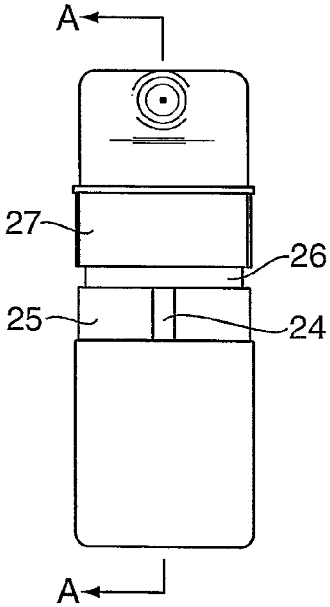
Figure 4:
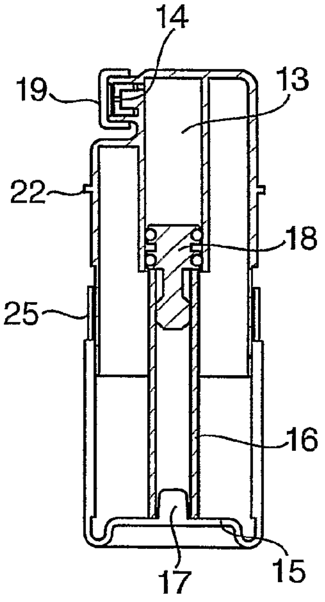
FIG. 4 is a section along the line a-a of FIG. 3.

In the two-dosage canister of the FIGS. 1 through 6 the circular-cylindrical top portion 11 of the canister telescopes within the similarly circular-cylindrical bottom portion 12. The top portion 11 as illustrated in FIG. 4 incorporates a circular-cylindrical chamber 13 into which the narcotic in fluid or powder form is packed. An orifice 14 is positioned adjacent the closed upper end of the top portion 11 of the canister and the canister contents are sprayed through this orifice to the atmosphere via a nozzle when the canister is activated.

The close end face 15 of the bottom portion of the canister is dished, as shown, and locates into an abuts one end of a tubular cylindrical piston rod 16. A spigot 17 is a push fit inside the end of the tubular piston rod 16 and locates the rod centrally on the recessed dished surface 15 of which the spigot 17 forms an integral protrusion.

The other end of the tubular piston rod 16 locates a piston 18 which is sized, and sealed to be a sliding fluid-tight push fit inside the chamber 13. The piston 18 when activated therefore acts to expel progressively the narcotic from the chamber 13 out via the orifice and nozzle 14.

Figure 5:
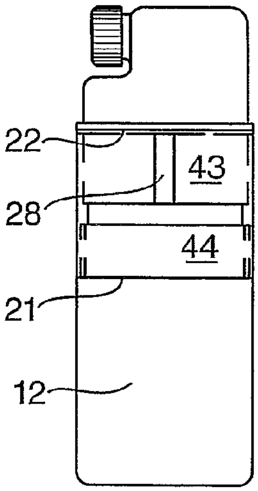
Figure 6:
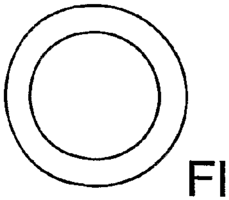

As initially supplied, the orifice and its nozzle are protected by a removable cap 19 and the gap between the radially outermost surface 21 of the canister base portion 12 and the radially outermost surface 22 of the top portion 11 is covered by 2 peelable plastics transparent tamper-evident sealing rings 23, 24 (shown in chain line in FIG. 5 that removed from each other figure). With the canister contents already packed into the chamber 13 and the piston and piston rod assembly in place, a one-way ratchet mechanism of the kind shown in FIG. 13 constrains the canister halves subsequent to the two halves being assembled.

The radially outermost surface of the bottom canister half 12 is formed with an inward-projecting key tab 23. This key is a sliding engagement fit in a guide groove 24 formed along the length of a ring 25 which is bonded to the surface of the canister half 11. The key 23 is of restricted longitudinal depth such that, as the two halves of the canister are brought towards one another by pushing the end face of one half towards the other, the key tab 23, when it has cleared the groove 24 axially can then move radially along a space 26 defined between the end of the ring 25 and the protruding portion of the canister top half 11.

Figure 1:
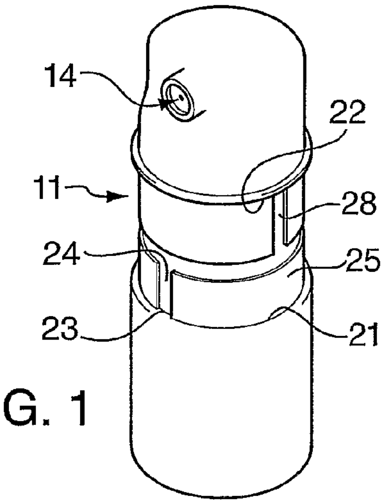
Figure 2:
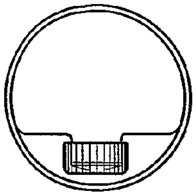

That protruding portion is labelled 27 in FIG. 3 of the drawings and it incorporates, as FIGS. 1 and 5 each show, its own longitudinal groove along which the key can again move when properly positioned to enter the groove 28.

For the key 23 to make these successive movements, it must first be sent along the groove 24 by virtue of the bottom canister half 12 being pushed towards the top canister half 11 as outlined above. The bottom half 12 must then be twisted radially about the top half 11 by 45° to move the key 23 along the defined space 26 and into alignment with another groove 28. Another axial push on the inface in of the bottom half of canister 12 sends the key 23 along the groove 28 until the radially outermost surface 21 of the canister half 12 is up against the underside of the radially outermost surface 22 of the top canister half 11.

These two successive movements will of course actuate the piston 18 to expel sequentially two successive doses of fluid from the chamber 13 via the spray-nozzle-containing orifice 14. The whole design of the canister makes it impossible for the second dosage to be dispensed before the first has been fully dispensed and also prevents the second dosage from being dispensed until after the twist-and-push action has been applied to the bottom canister half 12.

The one-way ratchet construction has the dual function, firstly of resisting any attempt to pull the two canister halves apart once they have been initially assembled and secondly of effectively locking the canister shut once both doses have been fully dispensed. The two circular-cylindrical canister halves are sufficiently resilient to allow the ratchet teeth to ride over one another in axial relative movement whilst being tough enough to resist at least initial attempts to puncture or break open the canister surfaces.

The protective cap 19 must of course be removed before any dose can be dispensed. As well as having a protective function to prevent dirt entering the nozzle, in preferred embodiments of the device, the cap is a sealing cap to prevent moisture ingress into the device, and to act as an additional safety feature in the unlikely event of leakage of the contents through the valve. The tamper-evident transparent plastics sealing rings 23 and 24 ideally should be removed in sequence 24 followed by 23, 24 alone being removed to dispense the first dosage and then 23 subsequently being peeled away when the second dosage is ready for dispensation.

The embodiment of FIGS. 8 through 12 differs principally from the one described above in that it is a one-dosage-only dispenser. The tamper sealing cover 29 of this embodiment occupies the whole of the gap between the radially outermost surface 31 of the top canister half and the radially outermost surface 32 of the bottom half. When the tamper seal 29 is broken and peeled off, a single push on the end face 33 of the canister along the central axis thereof dispenses the whole dose in one go.

Other differences seen in the embodiment are, firstly, that the removable cap 34 has a bayonet-style extension 35 and is itself a push fit, not a screw fit, on the dispensing orifice; and the cap is angled at approximately 75° to the central longitudinal axis of the canister, as is the dispensing orifice and nozzle so that an accurately directed dosage spray can be dispensed.

This latter feature is especially useful if the spray is to be sublingually directed and the canister is to be inverted (from the position as shown in the drawings) in order to deliver it.

The scope of the invention is defined in the claims that follow.

The invention claimed is:

1. A one dose at a time canister for dispensing fluid, the canister being non-pressurised, said canister comprising an orifice from which fluid is dispensed as a result of two surfaces of the canister moving, from a non-dispensing starting position, towards one another under the control of a user; said surfaces comprising the respective opposite end region surfaces of a two-portion canister one of whose portions telescopes within the other; wherein the canister incorporates a mechanism which, once a first dose has been dispensed, acts to prevent any subsequent attempted movement of the said surfaces into or towards their non-dispensing starting position, and wherein the telescoped canister portions incorporate a one-way ratchet mechanism, said ratchet mechanism comprising a first rack and a second rack, each rack comprising a plurality of teeth, wherein upon assembly, a plurality of the teeth from each rack are interengaged and wherein when a dose is dispensed, the two racks ride over each other in relative axial movement causing further teeth from each of the racks to become interengaged, and wherein once the ratchet mechanism is assembled to form the canister, it resists any subsequent attempt at disassembly.

2. A canister according to claim 1 wherein multiple doses can be dispensed after the first dose by imparting a twist-and-push relative movement to the canister surfaces each time a subsequent dose is desired to be dispensed.

3. A canister according to claim 2 wherein the last such twist-and-push movement locks the canister portions.

4. A canister according to claim 2 wherein the last such twist-and-push movement closes the orifice of the canister.

5. A canister according to claim 2 wherein the last such twist-and-push movement automatically ejects from the canister the portion thereof containing the orifice from which the fluid has been expelled.

6. A canister according to claim 2 wherein the canister portions push and twist about one common axis.

7. A canister according to claim 1 wherein the mechanism acting to prevent movement of the canister surfaces towards their non-dispensing starting position acts in line with the telescoping action of the canister portions.

8. A canister according to claim 1 wherein the mechanism acting to prevent any attempted movement of the canister surfaces into the non-dispensing starting position operates without fracturing any internal component of the canister.

9. A canister according to claim 1 wherein the mechanism acting to prevent any attempted movement of the canister imparts a twist-and-push relative movement to the canister surfaces each time a subsequent dose is desired to be dispensed, and in that such movement operates without fracturing any internal component of the canister.

10. A canister according to claim 1 wherein there is a band around the outside surface of the canisters, said band being removable in order to allow the canister portions to telescope and allow fluid to be dispensed.

11. A canister according to claim 10 wherein the band forms a tamper-evident seal on the canister.

12. A canister according to claim 1 wherein the telescoping canister portions are each of substantially constant width along their respective lengths.

13. A canister according to claim 1 wherein fluid is discharged at an angle to the axis along which the canister portions telescope.

14. A canister according to claim 13 wherein the angle is substantially a right angle.

15. A canister according to claim 13 wherein the angle is an acute angle when measured with reference to the fluid-dispensing movement of the telescoping canister portions.

16. A canister according to claim 15 wherein the acute angle is approximately 75°.

* * * * *